United States Patent
Anderson et al.

(10) Patent No.: US 7,070,739 B1
(45) Date of Patent: Jul. 4, 2006

(54) DETECTION AND CHARACTERIZATION OF MICROORGANISMS

(75) Inventors: Norman G. Anderson, Rockville, MD (US); N. Leigh Anderson, Washington, DC (US)

(73) Assignee: Large Scale Proteomics Corporation, Vacaville, CA (US)

( * ) Notice: Subject to any disclaimer, the term of this patent is extended or adjusted under 35 U.S.C. 154(b) by 0 days.

(21) Appl. No.: 09/571,290

(22) Filed: May 16, 2000

Related U.S. Application Data

(62) Division of application No. 09/265,541, filed on Mar. 9, 1999, now Pat. No. 6,254,834.

(60) Provisional application No. 60/077,472, filed on Mar. 10, 1998.

(51) Int. Cl.
*G01N 21/29* (2006.01)

(52) U.S. Cl. .................. 422/82.05; 422/68.1; 422/73; 422/82.08; 422/82.09; 422/99; 422/102; 422/104

(58) Field of Classification Search ............... 422/68.1, 422/73, 82.05, 82.06, 82.08, 82.09, 99, 102, 422/104; 436/10, 164, 172, 174, 177, 180
See application file for complete search history.

(56) References Cited

U.S. PATENT DOCUMENTS

| | | | |
|---|---|---|---|
| 3,468,474 | A | 9/1969 | Shoblom et al. |
| 3,481,712 | A | 12/1969 | Bernstein et al. |
| 3,916,205 | A | 10/1975 | Kleinerman |
| 3,957,653 | A | 5/1976 | Blecher |
| 4,003,834 | A | 1/1977 | Coombs |
| 4,106,907 | A | 8/1978 | Charlton et al. |

(Continued)

FOREIGN PATENT DOCUMENTS

| EP | 412431 A3 | 2/1991 |
|---|---|---|

(Continued)

OTHER PUBLICATIONS

N.G. Anderson et al., "Separation of Subcellular Components and Viruses by Combined Rate- and Isopycnic-Zonal Centrifugation," *Nat. Cancer inst. Monogr.* 21:253-283 (1966) (pp. 253-269), Figs 1-13.

(Continued)

*Primary Examiner*—Jill Warden
*Assistant Examiner*—Dwayne K. Handy
(74) *Attorney, Agent, or Firm*—John E. Tarcza; John C. Robbins; Thomas Gallegos

(57) ABSTRACT

A method for separating microorganisms, especially infectious agents, from a mixture by two dimensional centrifugation on the basis of sedimentation rate and isopycnic banding density, for sedimenting such microorganisms through zones of immobilized reagents to which they are resistant, for detecting banded particles by light scatter or fluorescence using nucleic acid specific dyes, and for recovering the banded particles in very small volumes for characterization by mass spectrometry of viral protein subunits and intact viral particles, and by fluorescence flow cytometric determination of both nucleic acid mass and the masses of fragments produced by restriction enzymes. The method is based on the discovery that individual microorganisms, such as bacterial and viral species, are each physically relatively homogeneous, and are distinguishable in their biophysical properties from other biological particles, and from non-biological particles found in nature. The method is useful for distinguishing infections, for identifying known microorganisms, and for discovering and characterizing new microorganisms. The method provides very rapid identification of microorganisms, and hence allows a rational choice of therapy for identified infectious agents. A particularly useful application is in clinical trials of new antibiotics and antivirals, where it is essential to identify at the outset individuals infected with the targeted infectious agent.

19 Claims, 9 Drawing Sheets

U.S. PATENT DOCUMENTS

| | | | |
|---|---|---|---|
| 4,214,993 A | | 7/1980 | Forsythe, Jr. et al. |
| 4,303,616 A | | 12/1981 | Kano et al. |
| 4,369,117 A | | 1/1983 | White |
| 4,403,861 A | * | 9/1983 | Boisde et al. ............... 356/407 |
| 4,436,631 A | | 3/1984 | Graham, Jr. et al. |
| 4,480,038 A | | 10/1984 | Cheng |
| 4,558,947 A | | 12/1985 | Wardlaw |
| 4,609,991 A | * | 9/1986 | Minton et al. ................ 702/25 |
| 4,624,835 A | | 11/1986 | Davis et al. |
| 4,695,431 A | | 9/1987 | Farrell |
| 4,717,660 A | | 1/1988 | Schulte |
| 4,861,477 A | | 8/1989 | Kimura |
| 4,865,812 A | | 9/1989 | Kuntz et al. |
| 4,871,248 A | * | 10/1989 | Hoffman ...................... 356/36 |
| 5,030,421 A | | 7/1991 | Muller |
| 5,106,187 A | * | 4/1992 | Bezanson .................... 356/73 |
| 5,125,737 A | * | 6/1992 | Rodriguez et al. ............ 356/39 |
| 5,183,740 A | * | 2/1993 | Ligler et al. ............... 435/7.32 |
| 5,236,604 A | | 8/1993 | Fiehler |
| 5,260,032 A | | 11/1993 | Muller |
| 5,277,873 A | | 1/1994 | Hsei |
| 5,342,790 A | | 8/1994 | Levine et al. |
| 5,422,018 A | | 6/1995 | Saunders et al. |
| 5,449,621 A | | 9/1995 | Klein |
| 5,453,832 A | * | 9/1995 | Joyce ......................... 356/338 |
| 5,488,469 A | | 1/1996 | Yamamoto et al. |
| 5,489,396 A | | 2/1996 | Bous |
| 5,512,490 A | * | 4/1996 | Walt et al. .................. 436/171 |
| 5,531,104 A | | 7/1996 | Futterer et al. |
| 5,552,310 A | | 9/1996 | Yoshikura et al. |
| 5,558,998 A | | 9/1996 | Hammond et al. |
| 5,599,503 A | * | 2/1997 | Manz et al. ............. 422/82.05 |
| 5,599,664 A | | 2/1997 | Schwartz |
| 5,632,905 A | | 5/1997 | Haynes |
| 5,853,894 A | | 12/1998 | Brown |
| 5,946,220 A | * | 8/1999 | Lemelson ................... 700/273 |
| 6,017,765 A | * | 1/2000 | Yamada et al. ............ 623/1.15 |
| 6,074,614 A | | 6/2000 | Hafeman et al. |
| 6,083,763 A | * | 7/2000 | Balch ......................... 436/518 |
| 6,252,236 B1 | * | 6/2001 | Trulson et al. ........... 250/458.1 |

FOREIGN PATENT DOCUMENTS

| | | |
|---|---|---|
| EP | 595641 A2 | 5/1994 |
| EP | 602416 A1 | 6/1994 |
| EP | 823633 A1 | 2/1998 |
| JP | 4036636 | 6/1992 |
| WO | WO 97/43621 | * 11/1997 |

OTHER PUBLICATIONS

G. Siuzdak, "Probing Viruses with Mass Spectrometry," *J. Mass Spectrometry* 33:203-211 (1998).

C.K. Tinkler et al., *The Chemistry of Petroleum and its Substitutes, A Practical Handbook*, Crosby Lockwood and Son, London, pp. 172-173 (1917).

R. Cross, "A Handbook of Petroleum, Asphalt and Natural Gas," Bulletin No. 25, Kansas City Testing Laboratory, Kansas City, MO, pp. 648-649 (1928 Revision).

*Tentative Method of Test for Water and Sediment by Means of Centrifuge*, ASTM Designation D96-50T (1950).

Fisher Scientific Catalog, p. 417 (1998).

* cited by examiner

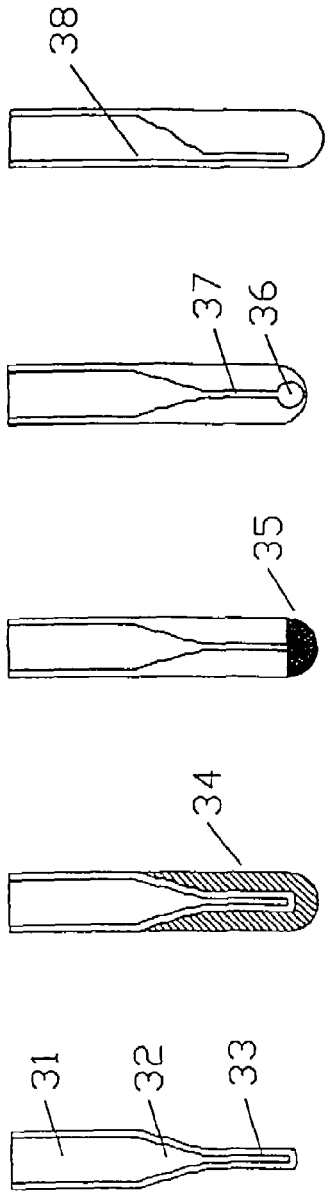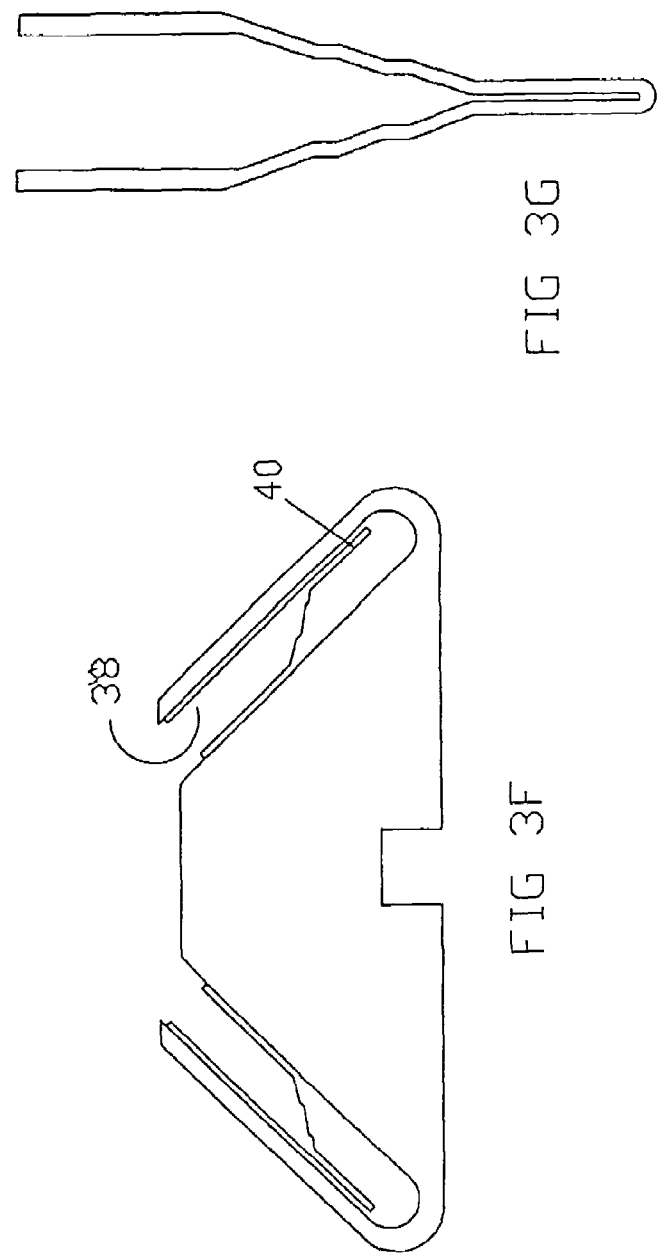

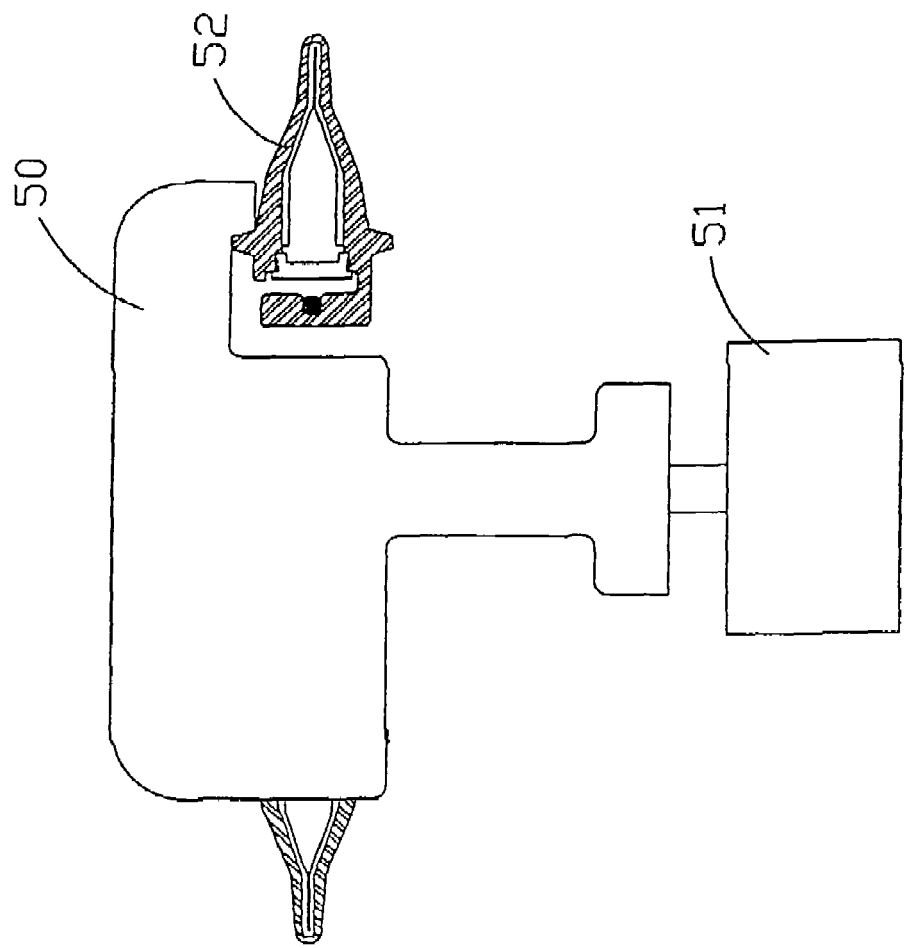
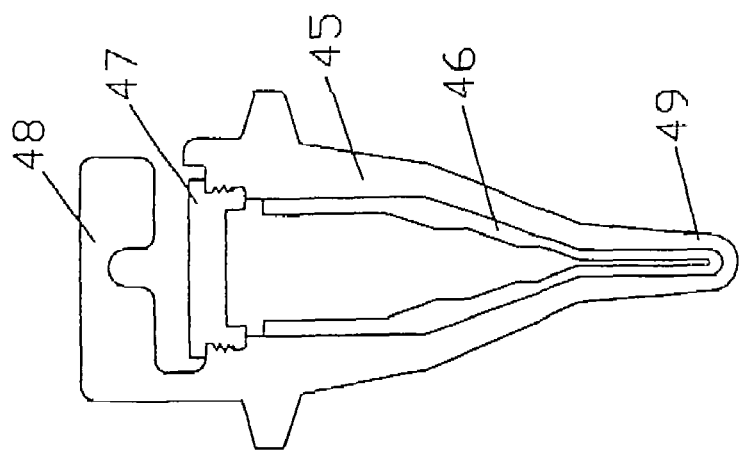
FIG 4B
FIG 4A

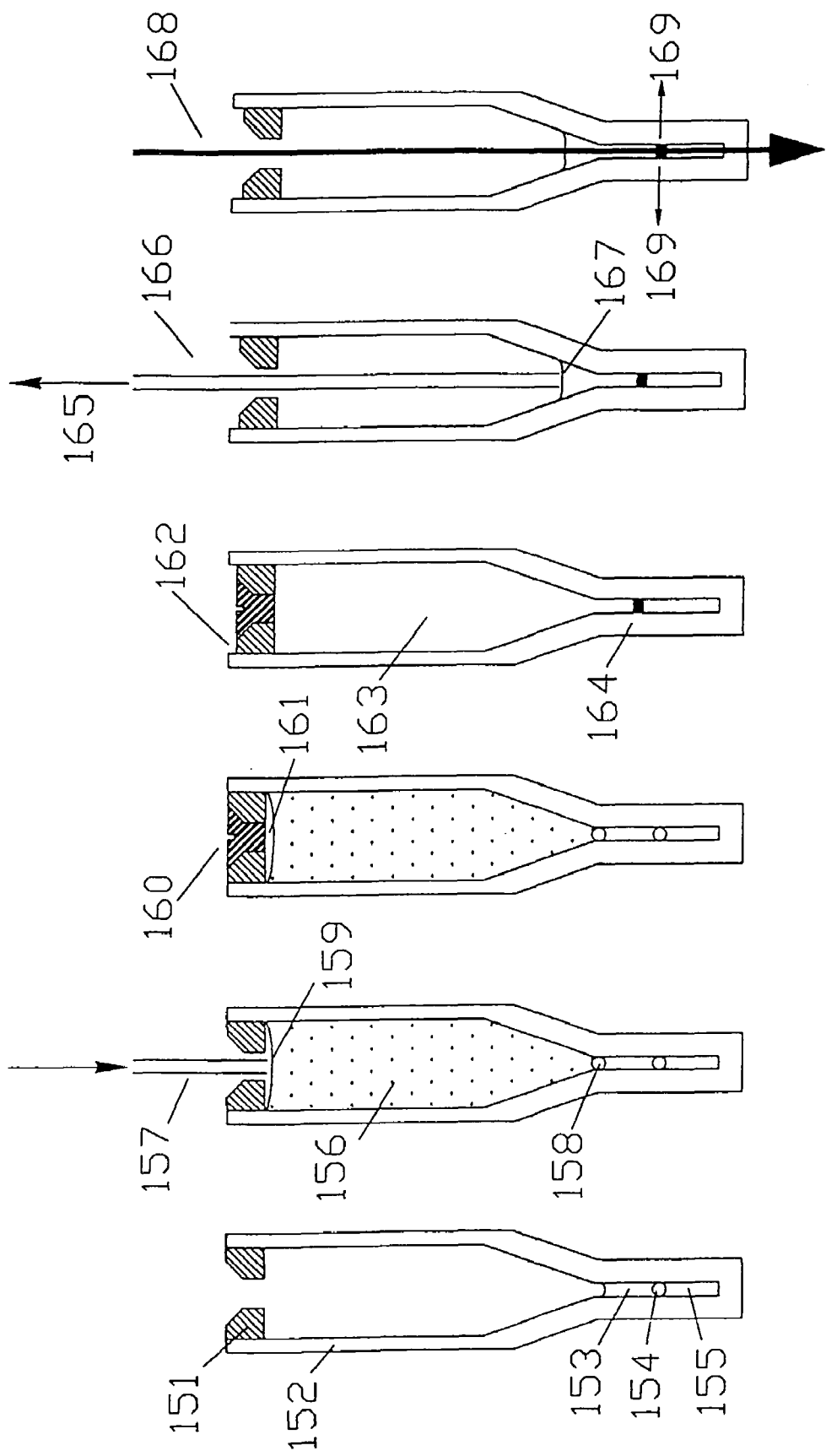

DETECTION AND CHARACTERIZATION OF MICROORGANISMS

CROSS-REFERENCE TO RELATED APPLICATION

The present application is a division of application Ser. No. 09/265,541, filed Mar. 9, 1999, now U.S. Pat. No. 6,254,834, which claims priority to U.S. provisional patent application Ser. No. 60/077,472, filed on 10 Mar. 1998, incorporated herein by reference.

This invention was made with Government support under an SBIR grants from NIH, Grant Nos. 1 R43 AI41819-01/02. The United States government may have certain rights in the invention.

BACKGROUND OF THE INVENTION

The present invention relates to the field of separating and identifying microorganisms, particularly infectious agents, using two-dimensional centrifugation and exposure to chemical and enzymatic agents, combined with detection in density gradients based on light scatter or fluorescence, counting by fluorescence flow cytometry, and characterization of intact virions, bacteria, proteins and nucleic acids by mass spectrometry, flow cytometry and epifluorescence microscopy.

The publications and other materials used herein to illuminate the background of the invention or provide additional details respecting the practice, are incorporated by reference, and for convenience are respectively grouped in the appended List of References. Patents referenced herein are also incorporated by reference.

In the prior art, diagnosis of viral and bacterial infections has been done by culturing the causal agents in suitable media or in tissue culture to obtain sufficient particles for analysis, followed by identification based on which conditions support growth, on reaction to specific antibodies, or based on nucleic acid hybridization (Gao and Moore, 1996). Biological growth can be omitted when the polymerase chain reaction (PCR) is used to amplify DNA, however, PCR requires sequence-specific primers, and is thus limited to known or suspected agents (Bai et al., 1997). For all these methods, considerable time is required, and the methods are useful for agents whose properties are known or suspected. Existing methods do not provide means for rapidly isolating and characterizing new infectious agents. Hundreds of infectious agents are known, and it is infeasible to have available reagents for an appreciable fraction of them.

Techniques for recovering infectious agents from blood, urine, and tissues have been previously developed based on centrifugation or filtration, but have not been widely used clinically (Anderson et al., 1966; Anderson et al., 1967). The highest resolution methods use rate zonal centrifugation to separate fractions based on sedimentation rate (measured in Svedberg units, S) and isopycnic banding density (measured in grams per mL or $\rho$). S-$\rho$ separations have been used to isolate virus particles in a high state of purity from rat liver homogenates, and have been used to isolate the equivalent of approximately 20 virions per cell (Anderson et al., 1966). In these studies, virus particles were detected by light scattering and visualized by electron microscopy. The separations required complex special equipment not generally available, one or more days of effort, and they did not provide a definitive identification of the bacterial or viral species separated.

It is important to show that candidate infectious particles isolated by centrifugal methods actually contain nucleic acids. DNA and RNA in both active and fixed bacterial and viral particles have been stained with fluorescent dyes specific to nucleic acids, and observed and counted by fluorescent microscopy and flow cytometry. Many dyes are now known which exhibit little fluorescence in the free state, but become highly fluorescent when bound to nucleic acids. Some bind differentially to DNA or RNA or to different specific regions, and some show different emission spectra depending on whether bound to DNA or RNA. In this disclosure, dyes referred to are fluorescent dyes. By differential fluorescence spectroscopy ssDNA, dsDNA and RNA may be distinguished. See, Haugland, 1996; Mayor and Diwan, 1961; Mayor, 1961; Hobbie et al., 1977; Zimmerman, 1977; Perter and Feig, 1980; Paul, 1982; Suttle, 1993; Hirons et al., 1994; Hennes and Suttle, 1995; Hennes et al., 1995.

Isolated nucleic acid molecules of the dimensions found in bacteria and viruses have been counted and their mass estimated using fluorescence flow cytometry for molecules in solution, and epifluorescence microscopy of immobilized molecules (Hennes and Suttle, 1995, Goodwin et al., 1993). In both instances, the size of fragments produced by restriction enzymes can be estimated, and the molecules identified by reference to a database listing the sizes of fragments of known DNA molecules produced by different restriction enzymes (Hammond et al., U.S. Pat. No. 5,558,998; Jing et al., 1998).

Using specific fluorescently-labeled antibodies, specific identifications may also be made. These studies are time consuming, and require batteries of specific antibodies, together with epifluorescent microscopy or fluorimeters.

Matrix-Assisted Laser-Desorption-Ionization Time-of-Flight Mass Spectrometry (MALDI-TOF-MS) currently allows precise measurements of the masses of proteins having molecular weights of over 50,000 daltons. Individual virion proteins have been previously studied by mass spectrometry (Siuzdak, 1998); however, resolution of complete sets of viral subunits from clinically relevant preparations of intact viruses, and the demonstration that precise measurements could be made of their individual masses, have not been previously reported. While single protein mass measurements can reliably identify many proteins, when a set of proteins from a virus or bacterial cell are known, detection of such a set provides more definitive identification. Methods are currently also being developed which allow partial sequencing of proteins or enzymatically produced peptide fragments and thus further increase the reliability of identifications. For MALDI-TOF-MS currently used methods require a picomole or more of protein, while electrospray mass spectrometry currently requires 5–10 femtomoles. The detection limits with mass spectrometry, especially MALDI, depend on getting a sample concentrated and on to a very small target area. Sensitivity will increase as ultramicro methods for concentrating and transferring ever smaller-volume samples are developed. See, Claydon et al., 1996; Fenselau, 1994; Krishmanurthy et al., 1996; Loo et al., 1997; Lennon and Walsh, 1997; Shevchenko et al., 1996; Holland et al., 1996; Liang et al., 1996.

Centrifugal methods for concentrating particles from large into small volumes have been in use for decades. Using microbanding centrifuge tubes which have a large cylindrical volume and cross section which tapers gradually in a centrifugal direction down to a small tubular section, particles may be concentrated or banded in a density gradient restricted to the narrow tubular bottom of the tube, or may be pelleted. The basic design of such tubes are well known by those skilled in the arts. See, Tinkler and Challenger, 1917; Cross, 1928; ASTM Committee D-2, 1951; Davis and Outenreath, U.S. Pat. No. 4,624,835; Kimura, U.S. Pat. No. 4,861,477; Levine et al., U.S. Pat. No. 5,342,790; Saunders et al., U.S. Pat. No. 5,422,018; Saunders, U.S. Pat. No. 5,489,396. The original tubes of this type were called Sutherland bulbs and were used to determine the water content of petroleum (The Chemistry of Petroleum and Its Substitutes, 1917, ASTM Tentative Method of Test for Water and Sediment by Means of Centrifuge, ASTM Designation: D 96-50T, 1947). Slight modifications of the basic design are described in U.S. Pat. Nos. 4,106,907; 4,624,835; 4,861, 477; 5,422,018, 5,489,396. Such tubes have been made of glass or plastic materials, and the use of water or other fluids to support glass or plastic centrifuge tubes in metal centrifuge shields has long been well known in the art. However, centrifuge tubes disclosed in the prior art which include a shape similar to that of the microbanding centrifuge tubes of the instant invention could not withstand the centrifugal forces required to band viral particles in gradients. Conventional centrifuge tubes, or tubes derivative from the Sutherland design have been used for density gradient separations, and for separations in which wax or plastic barriers are used which position themselves between regions of different density to allow recovery of these fractions without mixing. There has been no previous discussion of barriers which prevent mixing of step gradient components at rest, but which barriers are centrifuged away from the gradient during rotation. Nor have tube closures for high-speed thin-walled swinging-bucket centrifuge tubes been described, whose exterior surfaces can be disinfected after the tubes are loaded.

The efficient stabilization of very shallow density gradients in centrifugal fields is well known, and is utilized in analytical ultracentrifugation to cause a sample layer to flow rapidly to the centripetal surface of a gradient without mixing using a synthetic boundary cell (Anderson, U.S. Pat. No. 3,519,400). Hence, light physical barrier disks between step gradient components can be moved away from the gradient by centrifugal force without appreciably disturbing the gradient, provided that they are made of porous, woven or sintered materials having a physical density less than that of the sample layer, such as polyethylene or polypropylene.

Many authors have noted that viruses and bacteria are often resistant to the actions of detergents and enzymes which will digest or dissolve contaminating particles of biological origin, and efforts have been made to classify infectious agents on the basis of their differential sensitivities. These differences have not previously and conveniently been incorporated in a method for detecting and quantifying infectious agents. See, Gessler et al., 1956; Theiler, 1957; Epstein and Hold, 1958; Kovacs, 1962; Planterose et al., 1962; Gard and Maaloe, 1959. Density differences between different species of virus and bacteria are well known, but have not been previously exploited for purposes of identification.

Infectious particles exhibit a wide range of isopycnic banding densities ranging from approximately 1.17 g/ml to 1.55 g/ml, depending on the type of nucleic acid present, and the ratios between the amount of nucleic acid, protein, carbohydrate, and lipid present. While such banding density differences are well known, no attempt has been previously made to systematically measure them and use the data to classify infectious agents.

The present invention is directed to an integrated system for concentrating, detecting and characterizing infectious agents using separations based on sedimentation rate and banding density, spectral analysis of emitted fluorescent light to distinguish DNA from RNA, differentiation of viral and bacterial particles from other particles by sedimentation through zones of solubilizing enzymes or reagents, determination of the isopycnic banding densities of infectious particles by reference to the positions of synthetic density standardization particles, particle detection using fluorescent dyes for DNA or RNA, further concentration of banded particles by pelleting, transfer of concentrated particles to mass spectrometer targets for protein mass determination and analysis, counting of concentrated particles by epifluorescent microscopy and fluorescence flow cytometry, and identification of bacterial or viral nucleic acids by restriction fragment length polymorphism analysis using either immobilized nucleic acid molecules, or ultrasensitive fluorescence flow cytometry. These methods are especially useful in characterizing biological samples which have low titres of virus and which contain viruses which are not culturable.

Furthermore, all current methods used to detect and characterize infectious agents, including use of fluorescent antibodies, detection of agent-associated enzymes, culture to increase agent mass, PCR amplification, restriction fragment length polymorphism analysis, hybridization to probes immobilized on chips, histochemical analysis, and all forms of microscopy including electron microscopy, are vastly improved by preconcentration of the microorganisms using the methods of the present invention.

These techniques have not previously been assembled into one operational system capable of routine field, hospital, and clinical laboratory use. The present application describes innovations and inventions which make such a system feasible. For work with potentially lethal agents, the system will be assembled in containment, and at least partially automated.

SUMMARY OF THE INVENTION

The overall objective of this invention is to develop a physical system for rapidly identifying infectious disease agents without growing them, and for discovering new infectious agents. The process is based on the thesis that infectious agents constitute a unique group of particles which can be isolated by physical and chemical means from other natural particles and identified by their physical parameters using centrifugal means, fluorescence, and mass spectrometry. The system will allow rapid clinical distinction between viral and bacterial infections, identification of specific agents with the aim of providing specific therapy, and the rapid discovery of new infectious agents. In addition the system will make it feasible to develop and test new antibiotics and antiviral agents in man by measuring the effects of these agents on bacterial and viral loads. At present the development of new antiviral drugs is severely hindered by inability to define populations of individuals in the early stages of infection who might benefit from treatment.

In accordance with the present invention, an ultracentrifuge tube is provided which comprises upper, middle and lower regions of successively smaller diameters. In one embodiment, the tube has an upper region for receiving a sample, a funnel-shaped middle region and a lower narrow tubular microbanding region. The diameter of the lower region may be 0.25 inch or less, preferably 0.1 inch or less, more preferably 0.1 to 0.08 inch, and most preferably 0.08 to 0.039 inch. Smaller diameter microbanding regions are feasible and are within the province of this disclosure. The length of the lower region is typically between 5% to 25% of the length of the tube. In one aspect, the tube may also include a seal with a central opening which can be plugged and unplugged.

In accordance with the present invention, a bucket is provided for holding an ultracentrifuge tube. The bucket comprises upper and lower regions which may be of successively smaller diameters, may have inserts to successively decrease the inner diameter, or may be of uniform internal diameter, and may further comprise a third region which attaches the bucket to a rotor.

Further in accordance with the present invention, a method is provided for concentrating microorganisms. As used herein, the term "microorganisms" is intended to include viruses, myoplasmas, *rickettsia*, yeast and bacteria. The method comprises ultracentrifugation of a sample containing the microorganism in an ultracentrifuge tube described herein. The ultracentrifugation may include the formation of density gradients and/or the staining of the microorganism(s). In one aspect, the staining can be used to distinguish the DNA or RNA content of a virus. The banding of the microorganisms upon ultracentrifugation can be used to identify the microorganisms.

In a further aspect of the invention, the concentrated microorganisms are further characterized by conventional techniques such as mass spectrometry, flow cytometry, optical mapping, isopycnic banding densities, fluorescence, restriction enzyme analysis, genome size, enzymatic or chemical resistance/susceptibility, immunochemistry and the like. In another aspect of the invention, the amount or titre of the microorganisms can be determined.

In accordance with the present invention, a system is provided for measuring fluorescence from a sample in a centrifuge tube. In one embodiment, the system includes a centrifuge tube, a light source, such as a laser, and a detector to detect light passing through the sample or emitted from the sample upon light passing through it. Optical filters select and separate the exciting and emitted wavelengths of light.

The internal surfaces of the tubes and especially the funnel portion must be very smooth in order to prevent small virus particles from being retarded by surface irregularities, and in addition, the surfaces must be treated so that infectious particles are not adsorbed. Polishing of plastic surfaces is done by brief exposure to a solvent vapor. For example, polycarbonate is polished by brief exposure-to heated methylene chloride gas. Plastic surfaces are modified to prevent adsorption of infectious particles by exposure to dilute solutions of proteins such as bovine serum albumin or gelatin, or to charged polymers such as heparin or derivatives of heparin. Both of these procedures are well known to those practiced in the arts.

Further in accordance with the present invention, a system is provided for counting particles concentrated in a small volume. The system includes a container in which the particles are concentrated, a capillary tube, two pumps, means for moving the container relative to the capillary tube, a flow cell, a light source and detector. Alternatively, fluid may be moved by gas pressure instead of pumps.

BRIEF DESCRIPTION OF THE DRAWINGS

FIGS. 3A–3G show alternative embodiments of microbanding tubes and use in a rotor (3F).

FIGS. 4A and 4B illustrate a centrifuge swinging bucket design that allows higher speed fractionation of large sample volumes.

FIGS. 9A–9F illustrate one embodiment of a closure for swinging bucket rotor centrifuge tubes and detection of a sample with respect to the tubes.

DETAILED DESCRIPTION OF THE INVENTION

Figure 1:
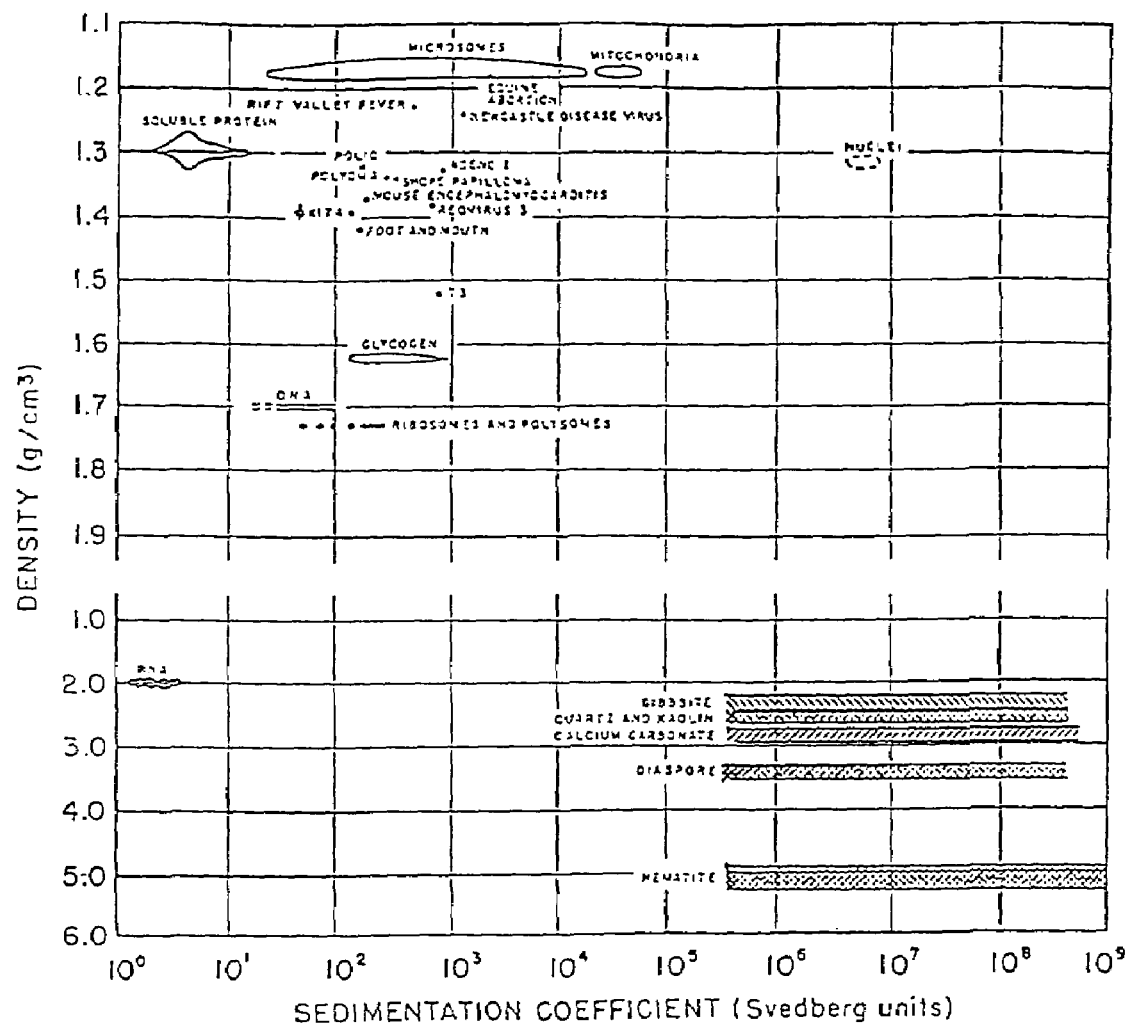
FIG. 1 shows an S-rho plot for a typical tissue and for representative viruses.

The invention is directed to methods of identifying and measuring the presence of microbial agents such as bacteria and viruses in biological samples. The methods include centrifugation steps to purify the microbial agents in a very small volume. The agents are then assayed by means such as isopycnic banding density, fluorescence or mass spectrometry.

It is an object of this invention to develop integrated systems and methods in which suspensions containing microorganisms, including infectious agents, are stained with one or more fluorescent dyes, in which a step or continuous gradient is automatically formed during centrifugation, in which the microorganisms are centrifuged away from the stain-containing suspending medium and are washed free of external stain, are concentrated in a gradient of very small cross section, separated according to their isopycnic banding densities, their banding densities determined, and the microorganisms detected by fluorescence.

It is a further object of this invention to concentrate microorganisms, including infectious agents, into microbands by a factor of 1–5,000.

It is a further object of this invention to expose the microorganisms, such as infectious agents, to reagents including detergents, surfactants, enzymes, or organic solvents contained in distinct zones in a density gradient to dissolve or disassemble contaminating particles to prevent them from banding with the microorganisms, and to separate stained particles from the free stain of the initial sample volume.

It is a further object of this invention to use one or more dyes which bind differentially to RNA, single stranded DNA or double stranded DNA to allow these to be distinguished by their fluorescent spectra.

It is a further object of this invention to provide for the concentration of banded microorganisms, for example infectious agents, by resuspending the banding gradient, which is typically 0.04 mL, to approximately 4 mL in water or a very dilute buffer, and pelleting the microorganisms one or more times to provide a concentrated pellet free of gradient materials for mass spectrometric analysis, for counting by epifluorescent microscopy or by flow cytometry.

It is a further object of this invention to provide means for the diagnosis of infectious diseases which minimize exposure of laboratory personnel to infectious agents.

It is an additional object of this invention to provide means for preparing nucleic acids from small quantities of microorganisms, including infectious agents, to determine the masses of intact nucleic acid molecules, and for characterization of fragments produced by restriction enzymes using either flow cytometry or epifluorescence microscopy.

It is an additional object of this invention to determine the banding densities of the microorganisms, such as infectious agents, accurately by reference to the positions of calibrated particles added to the gradients.

For ease of description, the invention will be described with reference to viruses as the microorganisms. It will be understood that the invention is also applicable to other microorganisms, including mycoplasmas, yeast and bacteria. The invention is particularly suited for the identification of infectious agents, and will be described in this context.

FIG. 1 is a graph depicting the sedimentation coefficients and isopycnic banding densities of subcellular organelles and viruses to illustrate the concept of the "Virus Window" (Anderson, 1966). It is evident that viruses have a relatively narrow range of sedimentation coefficients and banding densities and may be isolated from a tissue homogenate or from blood in a high state of purity using high resolution S-ρ separation systems. For a complete description of high resolution S-ρ centrifugal methods and of centrifuge development for virus isolation, refer to National Cancer Institute Monograph 21, The Development of Zonal Centrifuges and Ancillary Systems for Tissue Fractionation and Analysis, U.S. Department of Health, Education and Welfare, Public Health Service, 1966. This work describes S-ρ separation theory and systems, and the use of colored plastic beads of graded densities as density markers.

In practice, a blood sample or tissue homogenate is centrifuged to sediment all particles having sedimentation rates higher than that of the particle or particles to be analyzed. For viruses, that means particles of circa 10,000 S and above are discarded. The supernatant after such a separation is then used as the sample for second dimension isopycnic banding separations carried out in microbanding tubes as described here, using centrifugation conditions which will sediment and isopycnically band all known infectious particles.

One picomole of virus would contain $6.022 \times 10^{11}$ viral particles, while $6 \times 10^9$ virions would contain 1 picomole of a viral coat protein present in 100 copies per virion. Quantitative polymerase chain reaction (PCR) has been used to demonstrate that in many infectious diseases $>10^8$ virus particles are present per mL of plasma or serum. Hence, if the virions from a 5–10 mL biological sample containing $10^8$ virions/mL are concentrated to a microliter or two, and then applied to a very small target area, individual viral proteins can be detected using MALDI-TOF-MS (Krishmanurthy et al., 1996; Holland et al., 1966). Using electrospray techniques, samples containing $10^6$ virus particles/mL can be detected, while with flow cytometry and immobilized DNA epifluorescence microscopy, even fewer particles are required (Hara et al., 1991; Hennes and Suttle 1995). The application of these methods to bacteria may require a preseparation of proteins to reduce the complexity of the sample. In mass spectrometry, detection has been by charged ion detection, and the limitations of such detection have set the upper limits to the size of proteins and nucleic acids that can be detected. Mass spectrometric methods have now been described which allow masses of biological particles above 100,000 daltons to be measured.

Figure 2A:
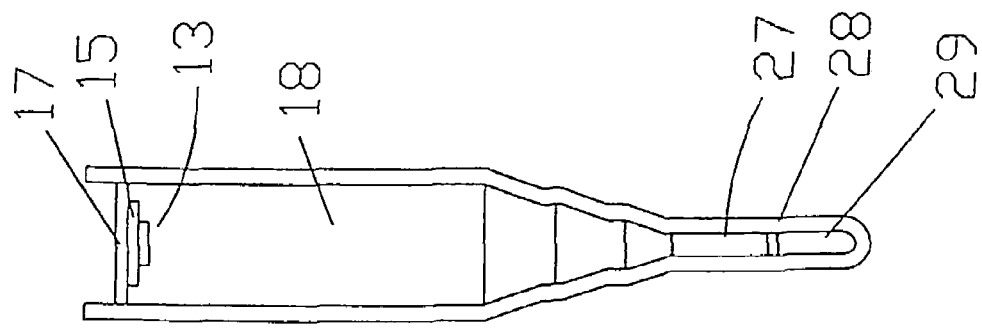
FIGS. 2A–2C are a diagrammatic representation of one embodiment of a centrifugal microbanding tube and its use.
Figure 2B:
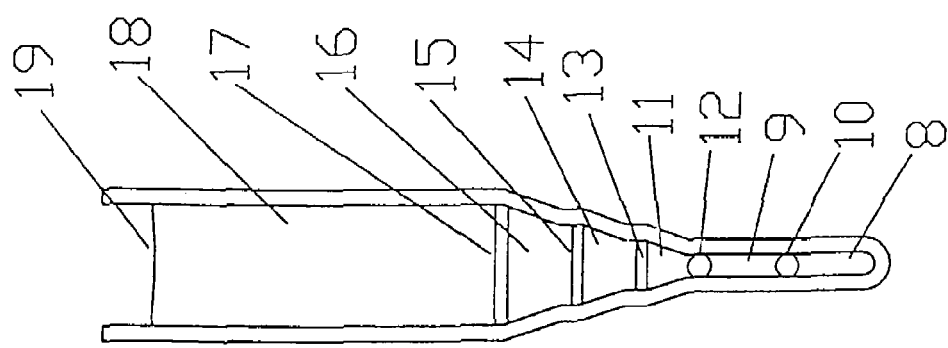
Figure 2C:
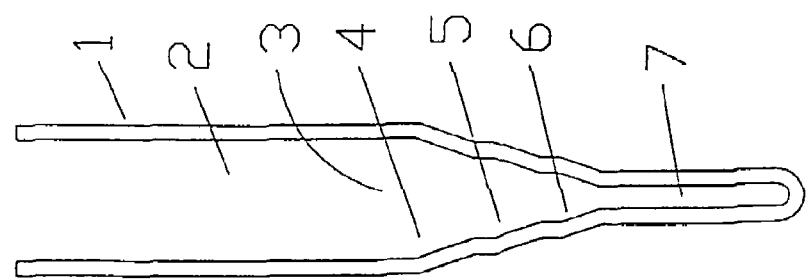
Figure 5:
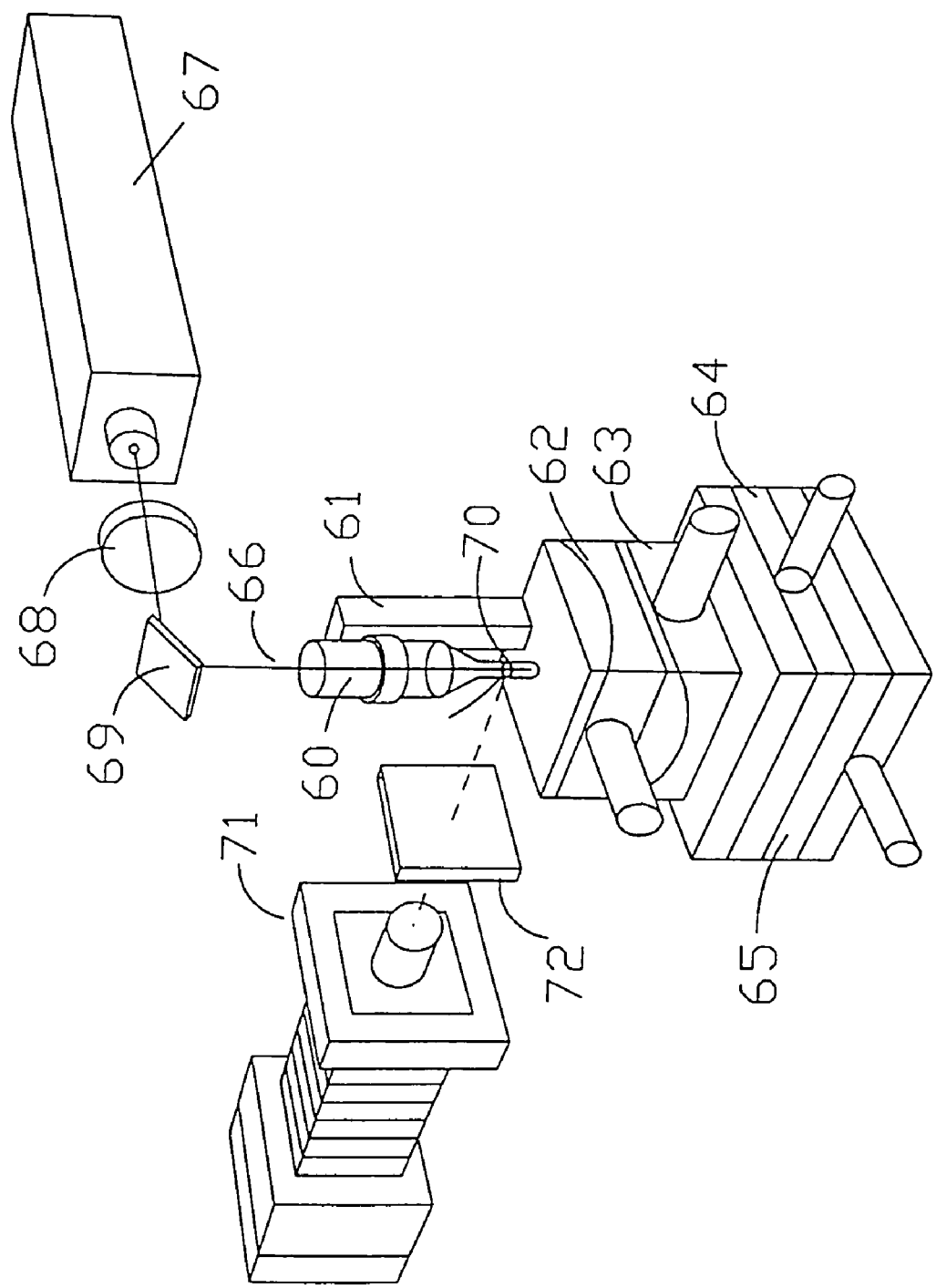
FIG. 5 illustrates a complete system including vertical monochromatric laser illumination, goniometer and X-Y stage for supporting and positioning microbanding tube, microbanding tube with banded viruses particles, and camera system.

In order to work with such levels of virus, the virus must be concentrated into a very small volume. This concentration is accomplished during the second dimension of centrifugation (the isopycnic banding step) by banding the virus using a centrifuge tube specially designed to concentrate the virus into a microband after passage through gradient layers that wash the particles and expose them to selected reagents. An example of such a microbanding centrifuge tube is shown in FIGS. 2A–2C. FIG. 2A illustrates diagrammatically a hollow transparent centrifuge tube 1 with an upper sample volume 2, grading into a serrated funnel region 3 having successively tapered and parallel-wall sections 4–6, constricting down to a narrow tubular microbanding region 7. The serrated funnel region 3 is an improvement over centrifuge tubes which simply taper from top to bottom without including a serrated region. By serrations is meant, for example, concentric rings or edges or lips. These rings, edges or lips are preferably continuous around the inner diameter of the centrifuge tube, but this is not required. For example, three projections from the inner wall of the centrifuge tube spaced equally around the diameter could be used to hold a disk in place. The term serrations is meant to include such possibilities but does not include a straight tapering with no rings, edges, lips or projections on the inner surface of the centrifuge tube. The serrations can be used as rests onto which disks can be placed to separate two or more layers of liquid. Although disks can be placed into tubes which simply taper without serrations, the disks in such tapered tubes can be easily tipped up on one edge by pushing down on the opposing edge. This would cause a premature mixing of the layers which are to be separated by the disks. The serrated region allows disks to lie flat and prevents the disks from being accidentally tipped up. As an example, the centrifuge tube may be 3.45 inches from top to bottom, have an outer diameter at the top of 0.562 inch, and have an inner diameter in the bottom microbanding region 7 of 0.064 inch. Such a tube is suitable for use in an SW41 Ti (Beckman) rotor. The inside surface of the tube is preferably polished using conventional techniques, including vapor polishing, so that the virus particles do not stick to the wall of the tube. Additionally, the internal surfaces of the tubes may be coated with a protein or polymer to prevent particle adhesion, as is well known in the art.

FIG. 2B illustrates how the tube is loaded at rest with a series of fluids of decreasing physical density. The tube shown comprises a series of serrations onto which can be laid disks to separate one layer of fluid from the next layer of fluid. Liquid 8 is denser than any particle to be recovered, and is used to partially fill the microbanding region 7. When a less dense fluid 9 is pipetted in with a micropipet an air bubble 10 (wherein by air is meant atmospheric air or another gas) may be left to keep the fluids 8 and 9 separate. Similarly when the first overlay fluid 11 is introduced, air bubble 12 may be left in place, thus keeping the three liquids separate until centrifugation is commenced. A tube with an inner diameter of 0.064 inches in microbanding region 7 is suitable for allowing an air bubble to be left in place to separate two layers of liquid. Alternatively, the air bubbles may be left out and the fluids allowed to diffuse together to create a density gradient. Fluid 11 is covered with a light porous plastic disk 13, preferably of sintered polyethylene or polypropylene, which fits in place in the first serration. A fluid 14, less dense than fluid 11, which may contain one or more reagents, is then introduced, and covered with disk 15, followed by even less dense liquid 16 which is covered with disk 17. The entire system is stable until centrifuged. Before use the sample layer 18, which has a density less than that of fluid 16 is then added up to level 19. The tubes are then centrifuged at high speed in metal shields, typically with water or other liquid added to the shields. In addition, the tubes may be supported by fitting adapters which fill the space between the tubes and the shields, and water may be added to fill any spaces between the tubes, adapters and shields to provide additional support. Optionally the tubes may be capped (as shown in FIGS. 9A–9F, described in further detail below), to minimize the chances of operator infection.

FIG. 2C illustrates diagrammatically a tube after centrifugation. The porous separation disks 13, 15, and 17 have risen to the top of the tube, and sample layer 18 is cleared of virus, and the original step gradient has changed, by diffusion, into one of a series of shallow gradients. In addition, gas bubbles 10 and 12 have also moved centripetally, and fluids 8 and 9 have come into contact to form a steep gradient by diffusion. As centrifugation proceeds, the slope of this gradient diminishes, producing a banding gradient of a width suitable for banding the infectious agents. For cesium chloride gradients, the densities typically range from 1.18 to 1.55 g/ml. These gradient steps may not only contain reagents to dissolve non-viral particles, but also serve to wash excess fluorescent dye away from the particles. For example, various detergents or enzymes such as proteases may be added either to the sample layer 18 or to other layers such as 14 or 16. Fluorescent dyes may also be present in these regions. The free dye will not enter the lower, more dense regions in which the virus bands and therefore the centrifugation will purify the viruses from all of the reagents which may be present in the upper, less dense layers. After centrifugation, the microbanding region of the tube contains the upper portion of the banding gradient 27, banded virus 28 (including any dye bound to the virus or viral nucleic acid) and lower dense portion of the banding gradient 29, and the gradient formed between them by diffusion.

FIGS. 3A–3G illustrate alternative embodiments of tubes useful for microbanding of viruses and bacteria and all have a serrated internal construction which allows one or more light barriers to be positioned and retained at rest. Tubes shown in FIGS. 3A–3D and 3G are designed to be centrifuged in swinging bucket rotors so that the tubes are horizontal during centrifugation and vertical at rest. The tube shown in FIG. 3A is the more conventional design with a sample reservoir 31, a serrated funnel region 32, and a microbanding section 33. The tube shown in FIG. 3B is similar to that of FIG. 3A, but it is supported in a centrifuge shield by a support insert 34 which may be of plastic or metal. The tubes shown in FIGS. 3B–3E fill a rotor chamber completely. The tube of FIG. 3C has an opaque bottom section 35 which absorbs scattered light, while that shown in FIG. 3D has a bulbous section 36 at the bottom of the microbanding tube 37 to contain an excess volume of the fluid forming the dense end of the gradient, thus stabilizing the gradient. The tube shown in FIG. 3E is designed to be centrifuged in an angle head rotor as shown in FIG. 3F, and has a linearly continuous wall 38 along one side positioned in the rotor so that particles may readily slide down to microbanding region 40. The tube shown in FIG. 3G illustrates how a very large microbanding tube may be fabricated.

FIGS. 4A–4B illustrate how the tube of FIG. 3G may be centrifuged at higher speed than tubes having a constant radius from top to curved bottom. This is accomplished by using a metal, plastic or carbon fiber shield 45 which matches the dimensions of tube 46. The shield has a cap 47 and the shield or bucket swings on integral attachment 48, as is conventionally done in high speed swinging bucket rotors. Tip 49 of the shield is much smaller diameter than the upper section of the shield, has much less mass swinging at its maximum radius, and hence can reach much higher speeds than is the case with shields of uniform internal diameter. This makes possible isolation of trace amounts of virus from much larger volumes than would otherwise be the case. During centrifugation using rotor 50 driven by drive 51, shield and tube 52 assume a horizontal position as shown.

The microbanded viruses can be analyzed at this stage or they can be collected, diluted, and further processed. To analyze the microbanded viruses at this stage, they can be detected by a system as shown in FIG. 5. For example, the isopycnic banding step or an earlier step may have included a fluorescent dye or fluorescent dyes within the solution with which the virus was mixed or through which the virus was centrifuged. Dyes are known with which intact viruses may be stained and which can distinguish between RNA, DNA, single stranded nucleic acid and double stranded nucleic acid thereby allowing one to detect the presence or absence of an infectious agent, and further to determine which type of virus one has purified. The apparatus of FIG. 5 can be used to analyze these stained particles.

A scanning and detection system is illustrated schematically in FIG. 5 where microbanding tube 60 is held in a vertical position on mount 61 supported by goniometers 62 and 63 which are in turn supported by X-Y movements 64 and 65 in such a manner as to align and center the microbanding section of tube 60 with respect to laser beam 66. Laser beam 66 is generated by a laser 67, which may be an argon ion laser producing coherent light at 458, 488, 496, 502, and 515 nm. The beam passes through an interference or other filter 68 to isolate one wavelength, and is reflected down into the microbanding tube by dichroic mirror 69. The fluorescent banded particle zone 70 is photographed or electronically scanned by camera 71 through emission filter 72. The entire system may be enclosed to eliminate stray light, and filters 68 and 72 may be replaced by filter wheels (not shown) to optimize detection using fluorescent dyes which absorb and emit at different wavelengths, or to distinguish ssDNA, dsDNA and RNA by differences in the spectra of emitted fluorescent light. Electronic shutters may be attached to the laser to minimize sample exposure to light and to the camera to control exposure. The goniometers and X-Y movements may also be motor driven and remotely controlled, and the entire system may be controlled by a computer (not shown).

FIG. 6 illustrates a different version of the scanning system which can cover all of the visible spectrum and on into the near ultraviolet. Microbanding tube 80 is aligned in a fixed support between transparent intensity equilibrators 81 and 82 attached to light pipes 83 and 84 which are in turn attached to intensity equilibrator 85 illuminated through filter 86 by condensing lens 87 and light source 88. Filter 86 is one of a set attached to filter wheel 89 indexed by motor 90. The result is uniform illumination from two sides of one or more bands 91, 92 and 93. The image is captured through emission filter 94 by digital camera 95 and the image stored, processed and displayed by computer 96 on CRT 97. Filter 94 may be replaced by a filter wheel identical to 89 and 90 so that, with both an excitation filter wheel and an emission filter wheel and a wide spectrum light source such as a xenon lamp or a halogen lamp, a wide variety of combination of exciting and emitting light may be chosen, which in turn makes possible use of a wide variety of fluorescent dyes. Both fluorescent light and light scatter at a chosen wavelength may be employed for particle detection. This arrangement facilitates distinction between ssDNA, dsDNA and RNA.

The processed image 98 may be displayed to show a picture of the tube and contained bands 99, 100 and 101. The amount of light from each band may be integrated and displayed as peaks 102, 103, and 104, and in addition the integrated values may be displayed digitally (not shown). The entire system including shutters on the light source and camera (not shown), filter movement and positioning, and focusing of the camera may be digitally controlled by computer 96.

Display bands 99 and 101, representing centrifuge tube bands 91 and 93 may be fluorescent or non-fluorescent density marker beads of known density, and the virus band 92 represented by display band 103. The banding density of the virus may be determined by interpolation from the positions of the density markers. When non-fluorescent density markers are used, these are detected by scattered light using identical filters at positions 86 and 94. A second image using suitable and different filters is then captured which is comprised solely of fluorescent light. The two images are electronically inter-compared and the physical density of the infectious agent determined by interpolation.

At this stage, the virus can be identified as being a DNA virus or an RNA virus, and if a DNA virus it can be determined whether it is single stranded or double stranded. Furthermore, the density of the virus can be determined. This data can be used to help identify the type of virus which has been purified. Nevertheless, it may be desirable or necessary to gather more data to fully determine what the exact virus is and also to determine the original viral titre.

Figure 7:
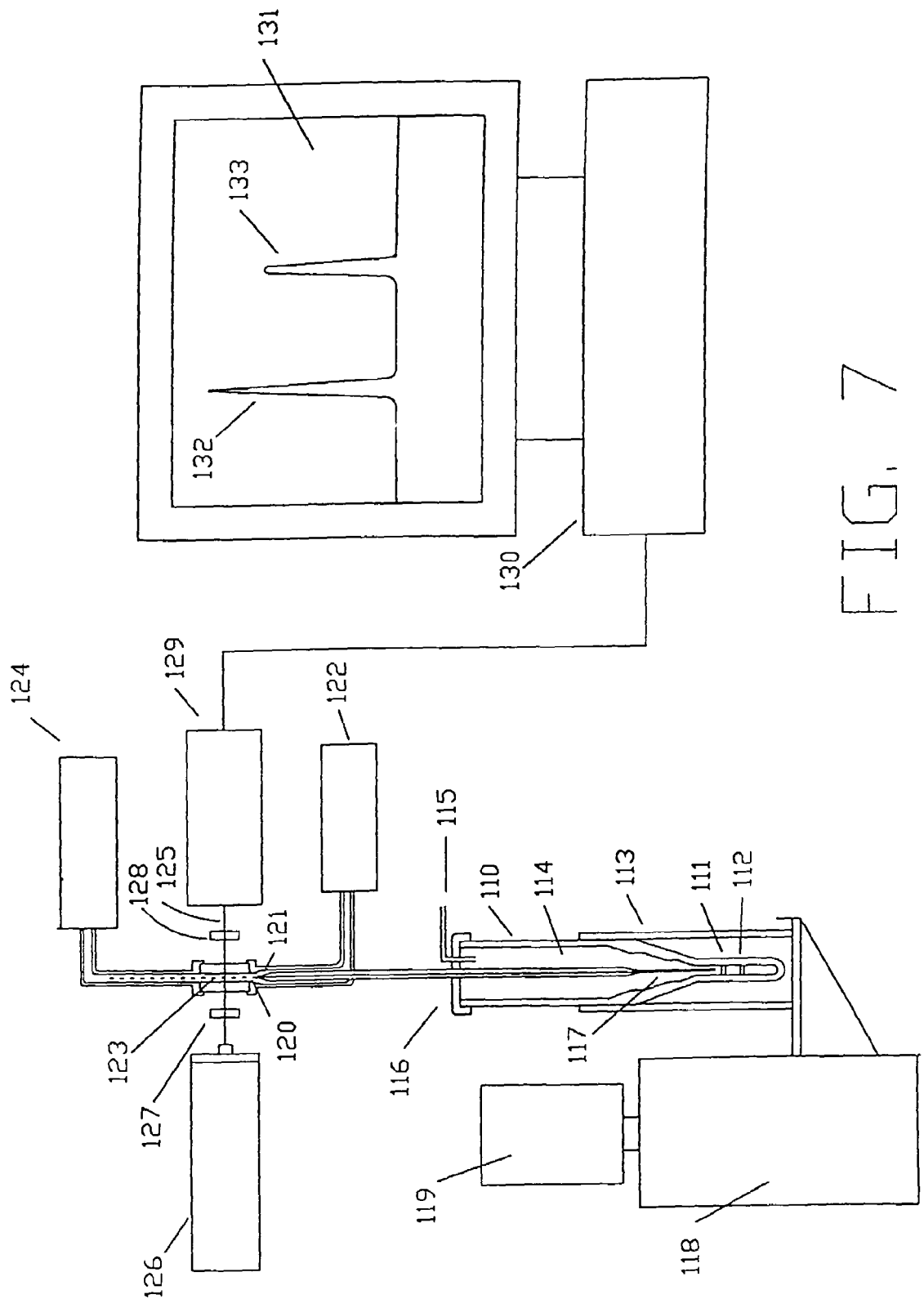
FIG. 7 illustrates a method for recovering banded virus particles using a micropipette, and counting them by flow cytometry.

FIG. 7 illustrates diagrammatically counting of individual fluorescent particles recovered from a tube 110 containing zones of banded virus 111 and 112 after all fluid above the banding gradient has been removed and replaced. The tube is placed in a tube holder 113, and an overlay of deionized water or very dilute buffer 114 is introduced above the gradient supplied through tube 115 to replace the volume drawn up in the probe 117. The tube may be closed at the top by a plastic closure 116. The capillary probe 117 is held stationary, and the microbanding tube 110 is slowly raised under it. The tube holder 113 is part of a precision drive mechanism 118 and associated stepping motor 119 that moves the tube holder vertically at a very slow and controllable rate. A slow steady stream of fluid is drawn into constriction 120 which is centered in sheath stream 121 provided by pump 122. The result is a constant flow of fluid through flow cell 123 with a fine virus containing stream in the center, elongated and extended by the flowing sheath. A second pump 124 withdraws fluid upward at a constant rate from the flow cell, which rate is greater than the rate at which piston pump 122 injects fluid into sheath 121. The difference in the rates of pumps 124 and 122 is made up by the fluid coming through capillary probe 117. The fluid coming through capillary probe 117 is a mixture of virus plus fluid from the overlay which is introduced via tube 115.

The flow cell 123 is illuminated by laser beam 125 produced by laser 126, that passes through exciting filter 127. Emitted light is isolated by emission filter 128 and detected by a photomultiplier 129. The output from the photomultiplier 129 is integrated at intervals by computer 130, and the integrated signal vs. time is displayed on CRT 131. When two viral bands are present, two peaks such as 132 and 133, are displayed. Depending on the number of fluorescent particles present, the signal generated from a band may be integrated into a peak, or, if the suspension is sufficiently dilute, the particles may be counted individually, the values binned, and the integrated results displayed.

Figure 8C:
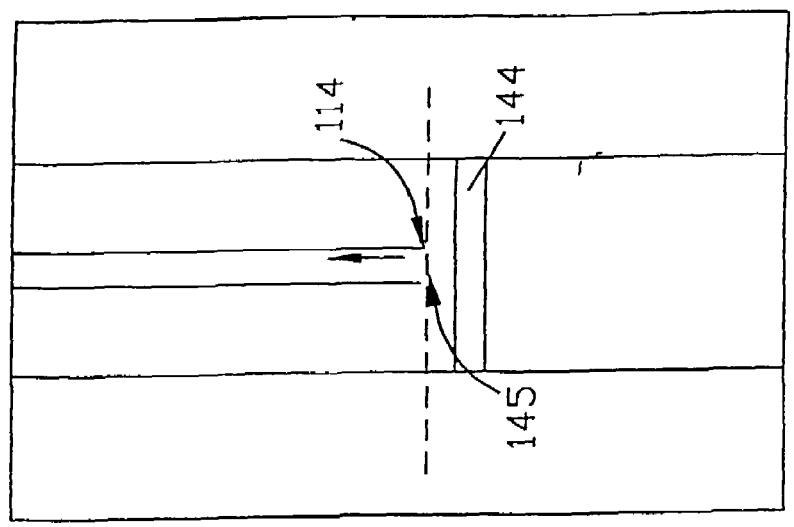
FIGS. 8A–8C illustrate details of band recovery.
Figure 8B:
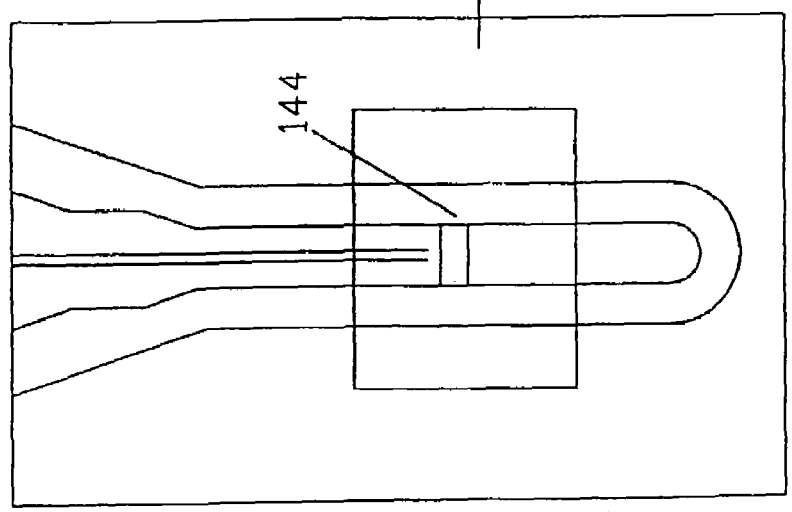
Figure 8A:
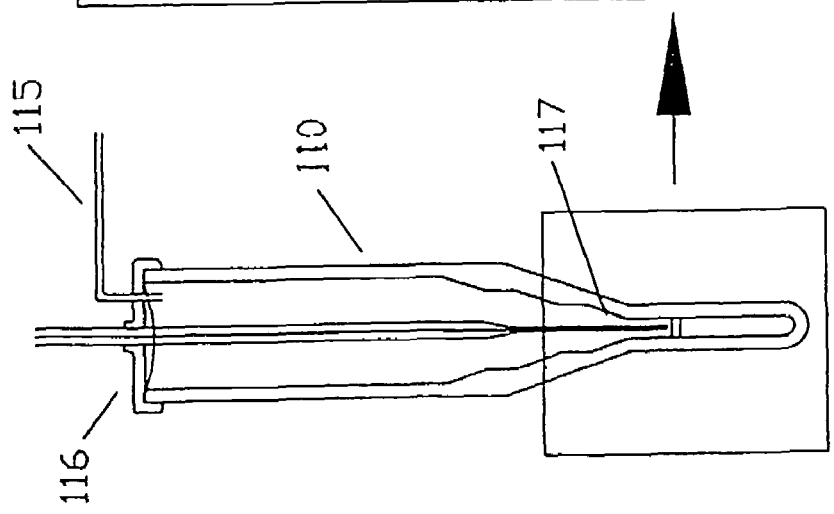

In order to count the particles as just described, it is necessary that the virus particles are greatly diluted as they pass through flow cell 123. FIG. 8 illustrates diagrammatically how the problem of making an initial dilution of a very small-volume virus band for counting individual particles is accomplished. FIG. 8A shows a tube 110 as in FIG. 7, with a section indicated which is shown enlarged in FIG. 8B, which in turn shows the section of that panel enlarged in FIG. 8C. As the movement upward of the microbanding tube causes the capillary tube to move toward the tube bottom, the difference in pumping rates of the two pistons attached to the flow cell causes fluid to flow up the capillary where it is diluted as described by the combined action of pumps 122 and 124 of FIG. 7. However, the amount of fluid drawn into the capillary 117 is much greater than the volume of fluid effectively displaced from the banding gradient by the relative movements of the capillary and the microbanding tube. This volume is replaced by fluid flowing into tube 115 though cap 116 which is initially allowed to flow in until the tube 110 is full. This fluid is much less dense than the density of the fluid at the top of the gradient in the microbanding region, and causes minimal disturbance in the gradient. As shown in FIG. 8B, the capillary 117 slowly approaches virus band 144, and, as shown in FIG. 8C, a small amount of gradient liquid 145 is diluted by a larger amount of supernatant fluid 114 as it flows up the capillary. In this manner, a sharp band of virus particles 144 is diluted and moves through the flow cell as, volumetrically, a larger band, but with little effective loss of resolution. This technique provides the dilution necessary to make counting of individual virus particles feasible and accurate. The amount of dilution can be controlled such that the concentration of microorganisms in the capillary tube is less than one-half or one-tenth, or one-hundredth, or one-thousandth, or one ten-thousandth, or one-millionth, or one-billionth of the concentration in the band in the lower region of said tube.

In addition to counting the particles or determining the titre of a virus, the amount of DNA in the virus or other microbe can be determined for individual particles. In this aspect of the invention, the amount of DNA in the particles is measured by flow fluorescence analysis (Goodwin et al., 1993) or epifluorescence analysis (Jing et al., 1998). In this manner, yeast, bacteria, mycoplasm and virus can be distinguished as groups, For example, it is known that viruses contain $5–200 \times 10^3$ bases or base pairs, *E. coli*, a typical bacterium, contains $4 \times 10^6$ base pairs, while a typical yeast cell contains $1.3 \times 10^7$ base pairs. Thus, an estimate of the amount of DNA or RNA present allows the class of an infectious agent to be determined.

Thus, the size of a genome can be determined. In this embodiment of the invention, the genome is extracted from the microorganism band and immobilized on a solid support. The immobilized DNA is stained and electronically imaged using an epifluorescence microscope (Jing et al., 1998). The length of the individual nucleic acid molecules can then be measured.

The technique of microbanding is useful not merely for staining the virus with dyes and being able to count the virus particles. Once the viruses from a biological sample have been highly purified and concentrated by the two dimensional centrifugation technique as described above using microbanding centrifuge tubes, the viruses are amenable for use in many other assays.

When an infectious agent is banded in a microbanding tube, the band may also be judiciously removed using a capillary needle in a volume of a few microliters, diluted to 5 mL or more with very dilute buffer or deionized water to dilute the gradient materials by a factor as large as 1,000, and then pelleted in a fresh microbanding tube. The supernatant may then be carefully withdrawn by a suction capillary, and the virus or other agent resuspended in approximately 1 microliter using a syringe made, for example, of fine Teflon® tubing fitted with a very small stainless steel wire plunger to fit. The sample may then be transferred to a mass spectrometer target, mixed with a matrix dye, and used for matrix assisted laser desorption ionization time of flight mass spectrometry (MALDI-TOF-MS) to determine directly the masses of viral coat proteins or of bacterial cell proteins. Technology described for sample concentration may also be applied, without a matrix dye, to electrospray or other mass spectrometric analysis systems, including the detection of intact viral mass.

A system similar to that shown in FIG. 7 may also be used to produce the equivalent of molecular restriction fragment length maps of DNA molecules using restriction enzymes. For this work, virus or bacterial particle bands may be diluted and sedimented as described, after which the DNA may be-extracted using detergents or other reagents well known in the art, treated with a restriction enzyme and a fluorescent dye, and the fragment sizes determined by flow cytometry (Goodwin et al., 1993; Hammond et al., U.S. Pat. No. 5,558,998). Extracted DNA may also be immobilized on a solid support, stained with a fluorescent dye, and photographed using an epifluorescence microscope to determine the length of DNA molecules. The preparation may then be treated with a restriction endonuclease, and the number and lengths of the oligonucleotide fragments determined (Jing et al., 1998). These data are then compared with a database listing the expected fragment lengths for different viral or bacterial species to identify each agent. DNA fragment lengths may also be determined by gel electrophoresis.

Fluorescence labeled antibodies may also be added to the particle suspension studied, and the presence or absence of the label in isopycnically banded particles determined. This approach is useful for specific identifications, and the use of a set of antibodies labeled with dyes having different and unique spectral characteristics allows the presence or absence of a series of agents to be determined. Alternatively antibodies labeled with chelators for rare earth's such as Europium and Terbium may be employed, in which case delayed fluorescence is measured.

Serum or plasma typically has a physical density between 1.026 and 1.031. Viruses typically have banding densities between 1.17 and 1.55 in cesium chloride, and at much lower densities in iodinated gradient materials such as Iodixanol or sucrose (Graham et al., 1994). The intermediate wash and reagent layers between the sample and the banding gradient must therefore have densities less than the density of the lightest virus to be banded. Buffers used to dissolve gradient material for virus isolation include 0.05 M sodium borate, and 0.02 M sodium cyanide, both of which prevent bacterial growth.

With human serum or plasma, centrifugation sufficient to remove platelets and other particles having sedimentation coefficients of approximately $10^4$ S is used before banding of virus particles.

The banding density of virus particles depends on the nucleic acid/protein ratio, and the presence or absence of lipids and lipoproteins. Hence attachment of specific identifying antibodies labeled with fluorescent dyes should not only allow identification by fluorescence but by a banding density change.

Figure 6:
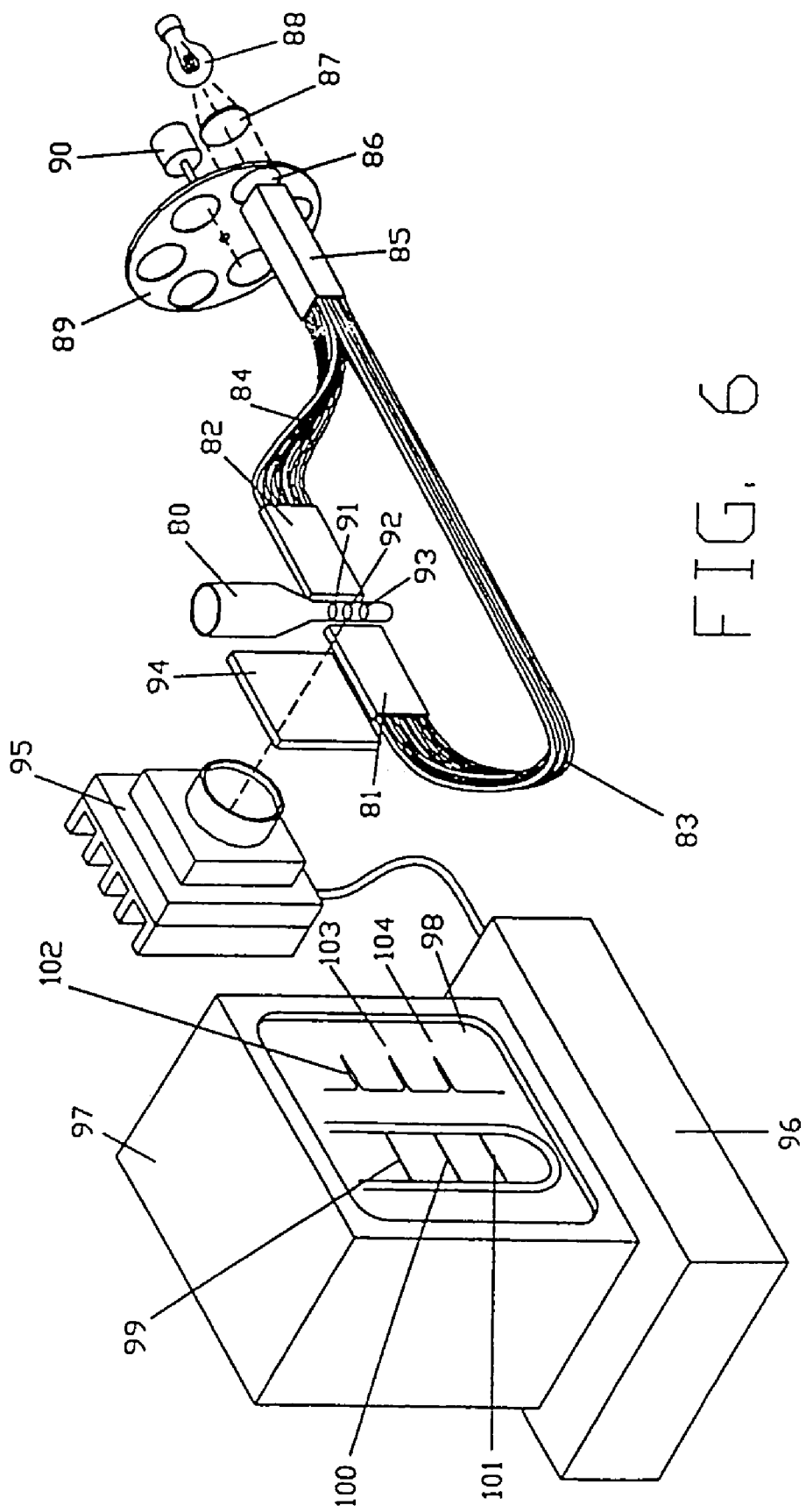
FIG. 6 illustrates a complete system including interference filter light sources, light pipe illumination, digital data acquisition, and CRT data presentation.

To assist in identifying particles by density, fluorescent particles of known density may be included in the sample as shown in FIG. 6. These particles may include known fixed and fluorescently stained virus or bacterial particles of known banding density, or very small fluorescently labeled or non-fluorescently labeled plastic beads. When polystyrene latex particles are coated with antibodies, their banding densities are increased appreciably, and the density may be further increased by reaction of the antibody-coated particles with the antigen for which the antibodies are specific (Anderson and Breillatt, 1971). Antibody-coated fluorescent polystyrene beads may therefore be used not only to locate virus particles but to identify them.

The stains which are currently most useful are described in the Handbook of Fluorescent Probes and Research Chemicals, R. P. Haugland, ed., Molecular Probes, Inc., Eugene, Oreg. (1996), which lists the abbreviated dye names, their chemical names, absorption and emission maxima, and the filter combinations most used.

For work with human pathogens, safe operation and containment are important (Cho et al., 1966). Use of swinging bucket rotors, while optimal from a physico-chemical point of view, require extensive manipulation and have more parts than an angle-head rotor. The tubes described in FIG. 3E are designed to be used in angle-head rotors, and allow sedimenting particles to travel along a wall at one unchanging angle. Such rotors are easier to use and handle in containment than are swinging bucket rotors, however, sedimentation in an angle head rotor is far from ideal. Hence, the development of methods and devices for safely working with swinging bucket rotors is important.

High speed centrifuge tubes are notoriously difficult to seal effectively and are a potential source of infection to laboratory personnel. In practice, nearly all high speed swinging bucket rotor tubes are not themselves sealed, but are enclosed in a metal bucket which is sealed with a metal cap which does not seal the tube. The centrifuge tubes are therefore open when loaded, moved to the centrifuge rotor, inserted, and removed. It is very difficult to decontaminate the outside of an open tube containing a density gradient without disturbing the gradient. In the present application it is desirable to be able to effectively seal the plastic tubes is such a manner that the outside surfaces can be cleaned with a suitable disinfectant before the tubes are inserted into centrifuge shields, and to be able to handle them safely until they are scanned.

Sealing is done, as shown in FIG. 9A, by inserting an annular ring seal 151, having a physical density less than that of water, into tube 152. Ring 151 is slightly tapered so that it fits very tightly into tube 152, and has a center hole which can be plugged and unplugged. In one embodiment, the center hole is threaded to accept a short, plastic flat-head screw. Initially two gradient components, including a lighter solution 153 and a denser solution 155, are introduced to the bottom microbanding region with a small air bubble 154 between, as previously described. As shown in FIG. 9B, the solution 156 containing the infectious agent or other particles is then introduced through tube 157, leaving bubble 158 to separate the sample from the upper gradient solution. The volume of sample introduced does not completely fill the centrifuge tube, leaving space 159 empty. The tube is then sealed, as shown in FIG. 9C with, for example, a plastic flat head screw 160, leaving air bubble 160 in place. The outside of the tube is then sterilized by immersing it in a disinfectant such as a sodium hypochlorite or hydrogen peroxide solution, followed by a water wash and gentle drying—all with the tube in an upright position. After centrifugation, as shown in FIG. 9D, the plastic upper seal has been driven downward by centrifugal force a small distance as the entrapped air rises around the plastic seal. However, since the seal has a density less than water, it is retained at the top of the liquid sample, leaving a small lip 160 which may be grasped with a hemostat to remove the tube from the centrifuge shield. During centrifugation, the infectious particles are sedimented out of liquid 163 and produce band 164 in the gradient. The screw in the ring seal is then removed, and, as shown in FIG. 9E, the supernatant liquid 165, which may contain a fluorescent dye, is removed through tube 166, leaving meniscus 167. As shown in FIG. 9F, a laser beam 168, entering the tube from above, is then aligned with the tube, causing the banded infectious agent to emit fluorescent light for detection as previously described.

When a step gradient containing various reagents in addition to those used for isopycnic banding is employed, as illustrated in FIG. 2, the discs used to separate the several solutions rise to the top and would not allow the use of vertical laser illumination as shown in FIG. 9F without removing the seal and the discs. In this instance, side illumination, as illustrated in FIG. 6 would be employed.

The laser or delayed fluorescence systems can be completely contained, the mechanical operations done remotely through small stepping motors, and the tubes moved in and out of the contained system under remote control.

These techniques can be combined with mass spectrometry and fluorescence-based restriction fragment mapping to allow rapid diagnosis and identification of infectious agents. However, the estimates of the masses of individual proteins are generally taken from published sequence data, and do not include numerous posttranslational modifications. Mass spectrometric data bases must be created to include actual mass measurements of different microorganisms. In addition, virion protein mass measurements will allow the detection of many genetic variants. However, for many studies of microorganisms, including development of data bases, the key problem has been the development of methods for systematically providing highly concentrated and purified microsamples of microorganisms from patient samples, natural waters, and from tissue culture fluids. This problem is solved by the present invention.

The present invention is described by reference to the following Example, which is offered by way of illustration and are not intended to limit the invention in any manner. Standard techniques well known in the art or the techniques specifically described below were utilized.

EXAMPLE

To illustrate the use of microbanding tubes, experimental studies have been carried out using a small single-stranded non-pathogenic DNA virus $\phi$X 174. Approximately $10^{10}$ virus particles which had been purified by isopycnic banding in CsCl in a microbanding tube such as shown in FIG. 2A were suspended in 5 mL of 0.05 M borate buffer, were pelleted in a microbanding tube at 35,000 rpm in a swinging bucket rotor, and were resuspended in approximately 3 μL for analysis. The analyses were done on a PerSeptive Biosystems DESTR instrument with an extraction delay time set at 150 nseconds using a matrix of sinapinic acid. Bovine insulin (Mw=5,734.59) and horse heart apomyoglobin (Mw=16,952) were used as 1 and 2 pmole standards. The results are shown in Table 1. The $\phi$X 174 masses for virion capsid proteins F, G, H and J are calculated from published sequence data. The differences between the calculated and experimental values for F and H are probably due to posttranslational modifications. The probability that an unrelated virus could have subunits of the same masses listed is vanishingly small. However, even more definitive protein identifications can be made by treating viral proteins with proteolytic enzymes such as trypsin and determining the masses of the peptide fragments produced. Computer programs are available which calculate the sizes of fragments of proteins of known sequence by well characterized enzymes. Such programs include Protein Prospector (available from the University of California, San Francisco) and ProFound (available from Rockefeller University).

TABLE 1

Mass Spectrometric Analysis of $\phi$X 174 Virion Proteins

| Protein | Calculated Mass | Experimental Mass | Mass Difference | % Difference |
|---------|-----------------|-------------------|-----------------|--------------|
| F | 48,351.53 | 48,407.4 | +55.9 | 0.12% |
| G | 19,046.73 | 19,046.7 | 0.0 | 0.00% |
| H | 34,419.25 | 34,466.1 | +46.9 | 0.14% |
| J | 4,095.78 | 4,097.03 | +1.2 | 0.03% |

This example demonstrates that highly purified and concentrated suspensions of microorganisms can be isolated from biological samples such as, but not limited to, patient samples such as plasma, urine, feces and tissues, natural water and tissue culture fluids. This example further demonstrates that such purified and concentrated microorganisms can then be identified, for example, using mass spectrometry to identify viruses.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Anderson, N. G., ed. (1966). "The Development of Zonal Centrifuges." *Natl. Cancer Inst. Monogr.* 21.

Anderson, N. G. et al. (1966). "Separation of subcellular components and viruses by combined rate- and isopycnic-zonal centrifugation." In *The Development of Zonal Centrifuges*. N. G. Anderson, ed. National Cancer Institute Monograph 21: 253–284.

Anderson, N. G. et al. (1967). "Isolation of viral particles from large fluid volumes." In *Transmission of Viruses by the Water Route*, G. Berg ed., Interscience Publishers, NY, pp. 75–88.

Anderson, N. G. (1968). "Analytical techniques for cell fractions. VIII. Analytical differential centrifugation in angle-head rotors." *Anal. Biochem.* 23: 72–83.

Anderson, N. G. and Breillatt, J. P. (1971). "Isopycnometric serology: A new technique based on buoyant density changes in latex beads." *Nature* 231: 112–114.

Bergh, O. et al. (1989). "High abundance of viruses found in aquatic environments." *Nature* 340: 467–468.

Borsheim, K. Y. et al. (1990). "Enumeration and biomass estimation of planktonic bacteria and viruses by transmission electron microscopy." *Applied Environ. Microbiol.* 56: 352–356.

Chang, Y. et al. (1994). "Identification of herpes virus-like DNA sequences in AIDS-associated Kaposi's sarcoma." *Science* 265: 1865–1869.

Cho, N. et al. (1966). "Problems in biocontainment." *Natl. Cancer Inst. Monogr.* 21: 485–502.

Claydon, M. A. et al. (1996). "The rapid identification of intact microorganisms using mass spectrometry." *Nature Biotechnology* 14: 1584–1586.

Fenselau, C. (ed.) (1994). "Mass spectrometry for the characterization of micro-organisms." *ACS Symposium Series*, Vol. 541, ACS, Washington D.C.

Fredricks, D. M. and Relman, D. A. (1996). "Sequence-based evidence of microbial disease causation: When Koch's postulates don't fit." *J. NIH Res.* 8: 39–44.

Gao, S.-J. and Moore, P. S. (1996). "Molecular approaches to the identification of unculturable infectious agents." *Emerging Infectious Diseases* 2: 159–167.

Goodwin, P. M. et al. (1993). "Rapid sizing of individual fluorescently stained DNA fragments by flow cytometry." *Nucl. Acids Res.* 21: 803–806.

Graham, J. et al. (1994). "The preparation of subcellular organelles from mouse liver in self-generated gradients of Iodixonol." *Anal. Biochem.* 220: 367–373.

Hara, S. et al. (1991). "Abundance of viruses in marine waters: Assessment by epifluorescence and transmission electron microscopy." *Applied Environ. Microbiol* 57: 2731–1734.

Harris, W. W. et al. (1966). "Unusual particles in human plasma from leukemia and lymphosarcoma." In *The Development of Zonal Centrifmuges. National Cancer Institute Monograph* 21: 289–394.

Haugland, R. P. (1996). *Handbook of Fluorescent Probes and Research Chemicals*, 6th ed. Molecular Probes Inc., Eugene Oreg., p. 679

Hennes, K. P. and Suttle, C. A. (1995). "Direct counts of viruses in natural waters and laboratory cultures by epifluorescence microscopy." *Limno. Oceanogr.* 40: 1050–1055.

Hennes, K. P. et al. (1995). "Fluorescently labeled virus probes show that natural virus populations can control the structure of marine microbial communities." *Applied Environ. Microbiol.* 61: 3623–3627.

Hirons, G. T. et al. (1994). "TOTO and YOYO: New very bright fluorochromes for DNA content analysis by flow cytometry." *Cytom.* 15: 129–140.

Holland, R. D. et al. (1996). "Rapid identification of intact whole bacteria based on spectral patterns using matrix assisted laser desorption ionization with time of flight mass spectrometry." *Rapid Commun. Mass Spectrom.* 10: 1227–1232.

Jing, J. et al. (1998). Automated high resolution optical mapping using arrayed, fluid-fixed DNA molecules. *Proc. Natl. Acad. Sci. USA* 95: 8046–51.

Kovacs, E. (1962). Chemical dissection of mammalian cells with liberation of biologically intact viruses. Z. Naturforschg. 17: 234–240.

Krishmanurthy, T. et al. (1996). "Detection of pathogenic and non-pathogenic bacteria by matrix assisted laser desorption ionization time of flight mass spectrometry." *Rapid Commun. Mass Spectrom.* 10: 883–888.

Liang, X. et al. (1996). "Determination of bacterial protein profiles by matrix assisted laser desorption ionization mass spectrometry with high performance liquid chromatography." *Rapid Commun. Mass Spectrom.* 10: 1219–1226.

Linnen, J. et al. (1996). "Molecular cloning and disease association of hepatitis G virus: a transfusion-transmissible agent." *Science* 271: 505–508.

Mazzone, H. M. (1998). CRC Handbook of Viruses. CRC Press, Boca Raton, p. 206.

Samad, A. H. et al. (1995). "Mapping the genome one molecule at a time—optical mapping." *Nature* 378: 516–517.

Simons, J. N. et al. (1995). "Identification of two flavi-virus-like genomes in the GB hepatitis agent." *Proc. Natl. Acad. Sci. USA* 92: 3401–5.

Siuzdak, G. (1998). Probing viruses with mass spectrometry. J. Mass Spec. 33: 203–211.

Suttle, C. A. (1993). "Enumeration and isolation of viruses." In *Handbook of Methods in Aquatic Microbial Ecology*, Chapter 15. Kemp, P. F., Sherr, B. F., Sherr, E. B. and Cole, J. J., eds. Lewis Publishers, Boca Raton, Fla., pp 121–134.

Suttle, C. A. and Chen, F. (1992). "Mechanisms and rates of decay of marine viruses in seawater." *Appl. Environ. Microbiol.* 58: 3721–3729.

Wommack, K. E. et al. (1992). "Distribution of viruses in the Chesapeake Bay." *Appl. Environ. Microbiol.* 58: 2965–2970.

Yolken, R. H. and Torrey, E. F. (1996). "Viruses, schizophrenia and bipolar disorder." *Clinical Microbiology Reviews* 8: 131–145.

Zeuzem, S. et al. (1996). "Phylogenetic analysis of hepatitis C virus isolates and their correlation to viremia, liver function tests, and histology." *Hepatology* 24: 1003–1009.

What is claimed is:

1. A system for counting particles which are concentrated in a small volume, wherein said system comprises:
   a container containing liquid in which said particles are concentrated in a localized area within the liquid;
   a capillary tube;
   a first pump and a second pump;
   means for moving said container relative to said capillary tube so that an end of the capillary tube passes into the container and through the liquid to the localized area containing said particles;
   a flow cell;
   a light source; and
   a detector
   wherein the capillary is capable of removing the localized area containing the particles from the container, and
   wherein said container comprises an upper centripetal region, a middle region and a lower centrifugal region, and wherein an inner diameter of said upper centripetal region of said container is larger than an inner diameter of said middle region and wherein an inner diameter of said middle region is larger than an inner diameter of said lower centrifugal region.

2. The system of claim 1, wherein said first pump pumps fluid into a sheath around an upper end of said capillary.

3. The system of claim 2, wherein said second pump pumps fluid out of said flow cell.

4. The system of claim 3, wherein said second pump pumps more fluid in a given time period than said first pump.

5. The system of claim 4, wherein fluid is drawn through a lower end of said capillary tube, said fluid exits said upper end of said capillary tube where it is surrounded by fluid pumped from said first pump, and wherein said second pump pumps a mixture of fluid exited from said upper end of said capillary tube and said fluid from said first pump through said flow cell.

6. The system of claim 5, wherein said light source produced a light beam which passes through said flow cell.

7. The system of claim 6 further comprising:
   a filter between said light source and said flow cell.

8. The system of claim 7 further comprising;
a filter between said flow cell and said detector.

9. A system for measuring light received from a sample banded in a localized area in a centrifuge tube wherein said system comprises;
a centrifuge tube;
a holder for said centrifuge tube in a vertical position so that liquid in the centrifuge tube is held stationary;
a light source to produce light capable of shining the light along a vertical length of the centrifuge tube, which will pass through said sample; and
a detector to detect light along a vertical length of the centrifuge tube passing from said sample which has been banded in a localized area, which is emitted from said sample,
wherein an internal cavity of said centrifuge tube comprises an upper region, a middle region and a lower region, wherein a diameter of said under region of said internal cavity is larger than a diameter of said middle region and wherein said diameter of said middle region is larger than a diameter of said lower region.

10. The system of claim 9, wherein said detector detects fluorescent light.

11. The system of claim 9, wherein said detector detects fluorescent light and wherein said system further includes a first filter positioned between said laser and said sample for isolating light of one wavelength and a second filter through which passes light emitted by an excited dye bound to said sample which has been banded in a centrifuge tube when said centrifuge tube is placed into said centrifuge tube holder.

12. The system of claim 9, wherein said detector detects scattered light.

13. The system of claim 9, wherein said detector detects scattered light and wherein said system further includes a filter positioned between said laser and said sample for isolating light.

14. The system of claim 1, wherein said detector detects fluorescent light.

15. The system of claim 1, wherein said detector detects scattered light.

16. The system of claim 1, wherein middle region of said container comprises one or more serrations.

17. The system of claim 9, wherein said light shines vertically along an entire vertical depth of the centrifuge tube and an entire vertical depth of the liquid in the centrifuge tube.

18. The system of claim 9, wherein the liquid in the centrifuge tube contains a density gradient.

19. The system of claim 1, wherein the liquid in the centrifuge tube contains a density gradient.

* * * * *